United States Patent [19]
Rast et al.

[11] Patent Number: 6,114,351
[45] Date of Patent: Sep. 5, 2000

[54] N-OXIDES AS ANTIBACTERIAL AGENTS

[75] Inventors: Hubert Rast, Leverkusen; Martin Scheer, Wuppertal; Werner Hallenbach, Monheim, all of Germany

[73] Assignee: Bayer Aktiengesellschaft, Leverkusen, Germany

[21] Appl. No.: 08/952,762

[22] PCT Filed: May 20, 1996

[86] PCT No.: PCT/EP96/02171

§ 371 Date: Nov. 19, 1997

§ 102(e) Date: Nov. 19, 1997

[87] PCT Pub. No.: WO96/38417

PCT Pub. Date: Dec. 5, 1996

[30] Foreign Application Priority Data

May 31, 1995 [DE] Germany .......................... 195 19 822

[51] Int. Cl.$^7$ .......................... A01N 43/42; C07D 215/16
[52] U.S. Cl. ............................. 514/312; 546/153
[58] Field of Search .............. 546/153; 514/312

[56] References Cited

U.S. PATENT DOCUMENTS 5,152,984  10/1992  Lange et al. .......................... 424/78.14

FOREIGN PATENT DOCUMENTS 90424  10/1983  European Pat. Off. .

OTHER PUBLICATIONS

Venezia et al., "In Vitro Activities of Amifloxacin . . . ", Antimicrobial Agents and Chemotherapy, vol. 33, No. 5, pp. 762–766, May 1989.

Journal of Medicinal Chemistry, vol. 27, No. 9, 1984, pp. 1103–1108, XP002012275, M.P. Wentland, et al.: "Novel amino–substituted 3–quinolinecarboxylic acid antibacterial agents".

Antimicrob. Agents Chemoth., vol. 33, No. 5, 1989, pp. 762–766, XP000600481, R.A. Venezia, et al.: "In vitro activities of amifloxaciin and two of its metabolites".

Chemical Abstracts, vol. 114, No. 13, 1991, Abstract No. 114663w, Y. Niwata, et al. "In vitro and in vivo antibacterial activity of urinary metabolites of fleroxacin" p. 22.

Chemical Abstracts Registry Handbook, XP002012276, Abstract No. 221823s, F. Collignon, et al. "In vitro models" p. 8, vol. 109, 1988.

Chemical Abstracts Registry Handbook, XP002012277, RN=106100–88–3, No. 413, 1987, pp. 199–206, G.R. Granneman, et al. "HPLC procedures for the determination of difloxacin and it metabolites".

Pathol. Biol. vol. 37, No. 5, 1989, pp. 406–410, XP000600482, J. Guibert, et al.: "Antibacterial activity of pefloxacin in urine".

*Primary Examiner*—Mukund J. Shah
*Assistant Examiner*—Tamthom N. Truong
*Attorney, Agent, or Firm*—Joseph C. Gil; Godfried R. Akorli

[57] ABSTRACT

The present invention relates to new antibacterial compositions, in particular orally administrable compositions, based on N-oxides of saturated nitrogen-containing heterocycles which are substituted by quinolonecarboxylic acids or naphthyridonecarboxylic acids, and to new active compounds and their preparation.

10 Claims, No Drawings

N-OXIDES AS ANTIBACTERIAL AGENTS

This is a 371 application of PCT/EP 96/02171 filed on May 20, 1996.

The present invention relates to new antibacterial compositions, in particular orally administrable compositions, based on N-oxides of saturated nitrogen-containing heterocycles which are substituted by quinolonecarboxylic acids or naphthyridonecarboxylic acids, and to new active compounds and their preparation.

N-oxides of saturated nitrogen-containing heterocycles which are substituted by quinolonecarboxylic acids are known as metabolites of the active compounds on which they are based. However, it is also known that these metabolites have no antibacterial action (J. Guibert et. al. Pathol. Biol. 1989, 37(5), 406–10; Venezia et. al. Antimicrob. Agents. Chemot. 1989, 33(5), 762–6).

It was further known that the oral administration of antibacterial compositions based on quinolone- or naphthyridonecarboxylic acids via the feed or drinking water of animals is often problematical. Refusal of drinking water or feed and thus an inadequate dose of the medicament often occurs. As medication via the feed or the drinking water is a very simple and stress-free type of administration for veterinary surgeon, animal keeper and animal to be treated, there is a high need for orally administrable compositions. It is desirable to be able to administer precisely the highly active antibacterial compositions of the quinolonecarboxylic acid series, such as enrofloxacin, reliably via the feed.

There have been found:

1. Antibacterial compositions based on N-oxides of saturated nitrogen-containing heterocycles which are substituted by quinolone- or naphthyridonecarboxylic acids of the formula (I) or (II):

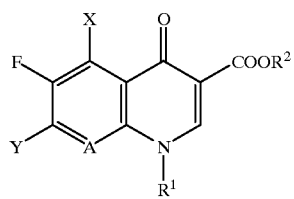
(I)

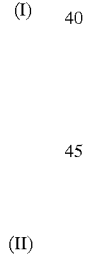
(II)

in which

X represents hydrogen, halogen, $C_{1-4}$-alkyl, $C_{1-4}$-alkoxy, $NH_2$,

Y represents radicals of the structures:

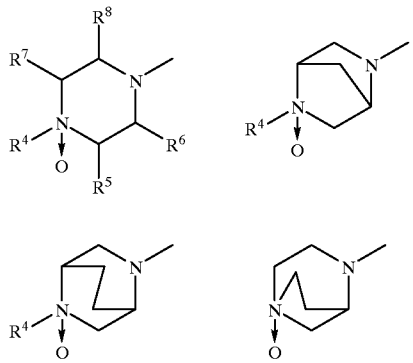

in which $R^4$ represents straight-chain or branched $C_1$–$C_4$-alkyl which is optionally substituted by hydroxyl or methoxy, cyclopropyl, acyl having 1 to 3 C atoms, $R^5$ represents hydrogen, methyl, phenyl, thienyl or pyridyl, $R^6$ represents hydrogen or $C_{1-4}$-alkyl, $R^7$ represents hydrogen or $C_{1-4}$-alkyl, $R^8$ represents hydrogen or $C_{1-4}$-alkyl, and $R^1$ represents an alkyl radical having 1 to 3 carbon atoms, cyclopropyl, 2-fluoroethyl, methoxy, 4-fluorophenyl, 2,4-difluorophenyl or methylamino, $R^2$ represents hydrogen or alkyl having 1 to 6 carbon atoms, which is optionally substituted by methoxy or 2-methoxyethoxy, and cyclohexyl, benzyl, 2-oxopropyl, phenacyl, ethoxycarbonylmethyl, pivaloyloxymethyl, $R^3$ represents hydrogen, methyl or ethyl and A represents nitrogen or =CH—, =C(halogen)—, =C(OCH$_3$)—, =C(CH$_3$)—, B represents oxygen, =N— which is optionally substituted by methyl or phenyl, and =CH$_2$, Z represents =CH— or =N—, and their pharmaceutically utilizable hydrates, acid addition salts and salts with bases. The compounds of the formulae I and II can be present in the form of their racemates or in enantiomeric forms.

2. Compositions administrable via the feed or drinking water of animals, based on N-oxides of saturated nitrogen-containing heterocycles which are substituted by quinolone- or naphthyridonecarboxylic acids, of the formulae (I) or (II):

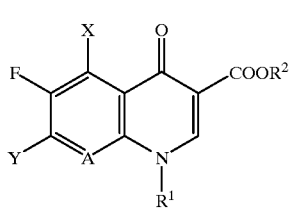
(I)

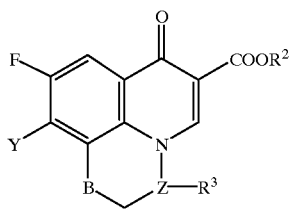

(II)

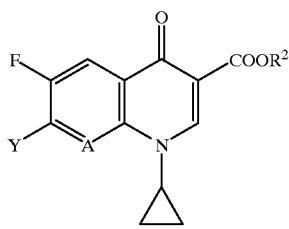

(Ia)

in which

Z and X have the meaning indicated above,

Y represents radicals of the structures:

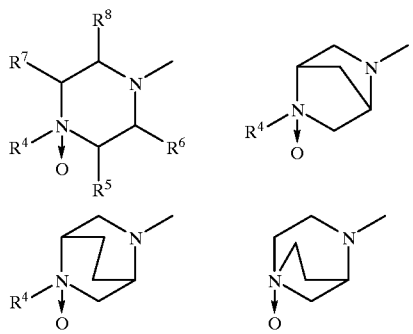

in which
- $R^4$ represents straight-chain or branched $C_1-C_4$-alkyl which is optionally substituted by hydroxyl or methoxy, cyclopropyl, acyl having 1 to 3 C atoms,
- $R^5$ represents hydrogen, methyl, phenyl, thienyl or pyridyl,
- $R^6$ represents hydrogen or $C_{1-4}$-alkyl,
- $R^7$ represents hydrogen or $C_{1-4}$-alkyl,
- $R^8$ represents hydrogen or $C_{1-4}$-alkyl, and $R^1$ represents an alkyl radical having 1 to 3 carbon atoms, cyclopropyl, 2-fluoroethyl, methoxy, 4-fluorophenyl, 2,4-difluorophenyl or methylamino, $R^2$ represents hydrogen or alkyl having 1 to 6 carbon atoms, which is optionally substituted by methoxy or 2-methoxyethoxy, and cyclohexyl, benzyl, 2-oxopropyl, phenacyl, ethoxycarbonylmethyl, pivaloyloxymethyl, $R^3$ represents hydrogen, methyl or ethyl and A represents nitrogen or =CH—, =C(halogen)—, =C(CH$_3$)—, =C(OCH$_3$), B represents oxygen, =CH$_2$ which is optionally substituted by methyl or phenyl, and their pharmaceutically utilizable hydrates, acid addition salts and salts with bases.

3. New N-oxides of saturated nitrogen-containing heterocycles which are substituted by quinolonecarboxylic acids, of the formula (Ia):

in which

Y represents radicals of the structures:

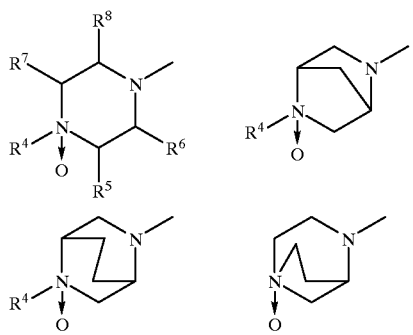

in which
- $R^4$ represents straight-chain or branched $C_1-C_4$-alkyl which is optionally substituted by hydroxyl or methoxy, cyclopropyl, acyl having 1 to 3 C atoms,
- $R^5$ represents hydrogen, methyl, phenyl, thienyl or pyridyl,
- $R^6$ represents hydrogen or $C_{1-4}$-alkyl,
- $R^7$ represents hydrogen or $C_{1-4}$-alkyl,
- $R^8$ represents hydrogen or $C_{1-4}$-alkyl, and $R^2$ represents hydrogen or alkyl having 1 to 4 carbon atoms, which is optionally substituted by methoxy, and benzyl, 2-oxopropyl, phenacyl and also ethoxycarbonylmethyl, A represents =N—, =CH—, =C(halogen)— or =C(OCH$_3$)—, and their pharmaceutically utilizable hydrates or acid addition salts or salts with bases.

It has furthermore been found that the compounds of the formula (Ia) are obtained when a) the corresponding compounds (III):

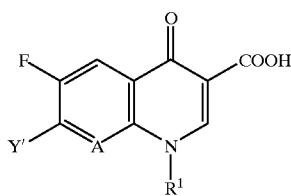

(III)

in which
Y' represents the saturated nitrogen-containing heterocycle on which the N-oxide radicals Z are based,
A and $R^1$ have the meaning indicated above, are reacted with oxygen-donating agents, or when b) compounds of the formula (IV):

in which
Z, A, $R^1$, $R^2$ have the meaning indicated above and
X denotes halogen, preferably fluorine or chlorine, are reacted with N-oxides of saturated nitrogen-containing heterocycles of the formula (V):

$$Y-H \qquad (V)$$

in which
Y has the meaning indicated above, if appropriate in the presence of acid binders.

Preferred compounds of the formula (I) are those in which
A represents =CH—,
$R^1$ represents $C_1$–$C_3$-alkyl which is optionally substituted by halogen, or cyclopropyl,
$R^2$ represents hydrogen or $C_{1-4}$-alkyl,
Y represents radicals of the structures:

in which
$R^4$ represents straight-chain or branched $C_1$–$C_3$-alkyl which is optionally substituted by hydroxyl, oxalkyl having 1 to 4 C atoms,
$R^5$ represents hydrogen, methyl or phenyl,
$R^7$ represents hydrogen or methyl, and their pharmaceutically utilizable hydrates and acid addition salts, and their alkali metal, alkaline earth metal, silver and guanidinium salts.

Particularly preferred compounds of the formula (I) are those in which

A represents =CH—,
$R^1$ represents cyclopropyl,
$R^2$ represents hydrogen, methyl or ethyl, Y represents radicals of the structures:

in which
$R^4$ represents methyl, ethyl which is optionally substituted by hydroxyl,
$R^5$ represents hydrogen or methyl,
$R^7$ represents hydrogen or methyl, and their pharmaceutically utilizable hydrates and acid addition salts, and the alkali metal, alkaline earth metal, silver and guanidinium salts of the carboxylic acids on which they are based.

Very particularly preferably, mention may be made of the N-oxides of the active compounds having the common names enrofloxacin, danofloxacin, ofloxacin, norfloxacin, benofloxacin, sarafloxacin, difloxacin, orbifloxacin, marbofloxacin.

In particular, mention may be made of the N-oxides of the active compounds enrofloxacin, marbofloxacin and ofloxacin.

If, according to method a) for the preparation of the new N-oxides, 1-cyclopropyl-7-(4-ethyl-1-piperazinyl)-6-fluoro-1,4-dihyro-4-oxo-quinoline-3-carboxylic acid and hydrogen peroxide are used as starting substances, the course of the reaction can be illustrated by the following reaction scheme:

If, for example, in the reaction according to method b), ethyl 7-chloro-1-cyclopropyl-6-fluoro-1,4-dihydro-4-oxo-quinoline-3-carboxylate and 1-ethylpiperazine N-oxide are used as starting substances, the course of the reaction can be illustrated by the following reaction scheme:

The quinolonecarboxylic acids or esters of the formulae (III) and (IV) used as starting substances according to methods a) and b) are known or can be prepared by known processes.

Examples which may be mentioned are:
1-ethyl-6-fluoro-1,4-dihydro-4-oxo-7-(4-ethyl-1-piperazinyl)-quinoline-3-carboxylic acid, 1-ethyl-6-fluoro-1,4-dihydro-7-(4-methyl-1-piperazinyl)-4-oxo-quinoline-3-carboxylic acid, 1-ethyl-6-fluoro-1,4-dihydro-4-oxo-7-(4-ethyl-1-piperazinyl)-1,8-naphthyridine-3-carboxylic acid, 9-fluoro-3-methyl-10-(4-methyl-1-piperazinyl)-7-oxo-2,3-dihydro-7,4-pyrido[1,2,3-di]-1,4-benzoxazine-6-carboxylic acid, 9-fluoro-5-methyl-8-(4-methyl-1-piperazinyl)-6,7-dihydro-1-oxo-1H, 5H-benzo[i,j]quinolicine-2-carboxylic acid, 6-fluoro-1-(4-fluorophenyl)-1,4-dihydro-4-oxo-7-(4-methyl-1-piperazinyl)-quinoline-3-carboxylic acid, 6-fluoro-1-(2-fluoroethyl)-1,4-dihydro-4-oxo-7-(4-methyl-1-piperazinyl)-quinoline-3-carboxylic acid, 1-ethyl-6,8-difluoro-1,4-dihydro-4-oxo-7-(4-methyl-1-piperazinyl)-quinoline-3-carboxylic acid, 1-cyclopropyl-6-fluoro-1,4-dihydro-4-oxo-7-(4-ethyl-1-piperazinyl)-quinoline-3-carboxylic acid, ethyl 1-cyclopropyl-6-fluoro-1,4-dihydro-4-oxo-7-(4-ethyl-1-piperazinyl)-quinoline-3-carboxylate, 1-cyclopropyl-6,8-difluoro-1,4-dihydro-4-oxo-7-(4-methyl-1-piperazinyl)-quinoline-3-carboxylic acid, 1-cyclopropyl-8-chloro-6-fluoro-1,4-dihydro-4-oxo-7-(4-methyl-1-piperazinyl)-quinoline-3-carboxylic acid, 1-cyclo-propyl-8-chloro-6-fluoro-1,4-dihydro-4-oxo-7-(4-methyl-1-piperazinyl)-quinoline-3-carboxylic acid, ethyl 7-chloro-1-ethyl-6-fluoro-1,4-dihydro-4-oxo-quinoline-3-caraboxylate, ethyl 1-ethyl-6,7-difluoro-1,4-dihydro-4-oxo-quinoline-3-carboxylate, ethyl 7-chloro-1-ethyl-6-fluoro-1,4-dihydro-4-oxo, 1,8-naphthyridine-3-carboxylate, ethyl 9,10-difluoro-3-methyl-7-oxo-2,3-dihydro-7,4-pyrido[1,2,3-de]-1,4-benzoxacine-6-carboxylate, ethyl 8,9-difluoro-5-methyl-6,7-dihydro-1-oxo-1H,5H-benzo[i,j]quinolicine-2-carboxylate, ethyl 7-chloro-6-fluoro-1-(4-fluorophenyl)-1,4-dihydro-4-oxo-quinoline-3-carboxylate, ethyl 6,7,8-trifluoro-1-(4-fluorophenyl)-1,4-dihydro-4-oxo-quinoline-3-carboxylate, ethyl 7-chloro-1-cyclopropyl-6-fluoro-1,4-dihydro-4-oxo-quinoline-3-carboxylate, methyl 7-chloro-1-cyclopropyl-6-fluoro-1,4-dihydro-4-oxo-quinoline-3-carboxylate, n-butyl 7-chloro-1-cyclopropyl-6-fluoro-1,4-dihydro-4-oxo-quinoline-3-carboxylate, ethyl 1-cyclopropyl-6,7-difluoro-1,4-dihydro-4-oxo-quinoline-3-carboxylate, ethyl 1-cyclopropyl-6,7,8-trifluoro-1,4-dihydro-4-oxo-quinoline-3-caraboxylate, ethyl 8-chloro-1-cyclopropyl-6,7-difluoro-1,4-dihydro-4-oxo-quinoline-3-carboxylate, ethyl 1-cyclopropyl-7-chloro-6-fluoro-1,4-dihydro-4-oxo-1,8-naphthyridine-3-carboxylate.

The amines of the formula (III) used as starting compounds are known. Chiral amines can be employed both as racemates, and as enantiomerically or diastereomerically pure compounds.

Further examples which may be mentioned are:
1-methylpiperazine,
1-ethylpiperazine,
N(2-hydroxyethyl)-piperazine,
N(2-methoxyethyl)-piperazine,
1-cyclopropylpiperazine,
1-phenylpiperazine,
1,2-dimethylpiperazine,
2,5-diazabicyclo[2.2.1]heptane,
2-methyl-2,5-diazabicyclo[2.2.1]heptane,
2,5-diazabicyclo[2.2.2]octane,
2-methyl-2,5-diazabicyclo[2.2.2]octane,
1,4-diazabicyclo[3.2.1]octane.

In the reaction of the compounds of the formula (III) with oxygen-donating agents, the compounds (III) are employed as such or in the form of their salts, such as mesylates.

The following oxygen-donating agents may be mentioned specifically:

Hydrogen peroxide, oxygen, organo-hydroperoxides such as tert-butyl hydroperoxide, cumene hydroperoxide. In this case the addition of a metal catalyst can be favourable (Mo, V, Ti).

Peracids: such as performic acid, peracetic acid, perbenzoic acid, monoperphthalic acid, sulphomonoperacid.

Peroxides such as benzoyl peroxide, perborate, percarbonate.

Ozone

The reaction temperatures can be varied within a relatively large range. In general the reaction is carried out between −20° C. and 200° C., preferably between 20° C. and 150° C.

The reaction can be carried out at normal pressure, but also at elevated pressure. In general, the reaction is carried out at pressures between 1 bar and 100 bar, preferably between 1 and 10 bar.

The reaction is preferably performed in a diluent.

The diluents used are all inert organic solvents. These include, in particular, aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, furthermore ethers such as diethyl ether and dibutyl ether, glycol dimethyl ether and diglycol dimethyl ether, tetrahydrofurane and dioxane, nitriles, such as acetonitrile and propionitrile, benzonitrile, glutaronitrile, moreover amides, such as dimethylformamide, dimethylacetamide and N-methylpyrrolidone, and also tetramethylene sulphone and hexamethylphosphormide, furthermore alcohols such as methanol, ethanol, n- and i-propanol, glycol monomethyl ether and water. Mixtures of these diluents can also be used.

The reaction can be carried out in the presence of auxiliary bases such as alkali metal and alkaline earth metal hydroxides (Li, Na, K, Mg, Ca) alkali metal and alkaline earth metal carbonates and hydrogen carbonates (Li, Na, K,) phosphates, salts of organic acid such as Na acetate.

When carrying out the process according to the invention, 1 to 15 mol, preferably 1 to 6 mol, of the oxygen-donating agent are employed relative to 1 mol of the compound (III).

The working-up of the reaction mixture is carried out in a manner known per se. If peracids are used as oxidizing agents, the corresponding acid addition salts of the compounds (I) and (II) can be obtained directly:

e.g. enrofloxacin+peracetic acid→enrofloxacin N-oxide acetate.

The acid addition salts of the compounds according to the invention are prepared in a customary manner, for example by dissolving the betaine in an adequate amount of aqueous acid and precipitating the salt using a water-miscible organic solvent such as methanol, ethanol, acetone or acetonitrile. Equivalent amounts of betaine and acid can also be heated in water or an alcohol such as glycol monoethyl ether and then evaporated to dryness or the precipitated salt filtered off with suction. Pharmaceutically utilizable salts are to be understood as meaning, for example, the salts of hydrochloric acid, sulphuric acid, acetic acid, glycolic acid, lactic acid, succinic acid, citric acid, tartaric acid, methanesulphonic acid, 4-toluenesulphonic acid, galacturonic acid, gluconic acid, embonic acid, glutamic acid or aspartic acid. The compounds according to the invention can also be bound to acidic or basic ion exchangers.

The alkali metal or alkaline earth metal salts of the carboxylic acids according to the invention are obtained, for example, by dissolving the betaine in a substoichiometric amount of alkali metal or alkaline earth metal hydroxide solution, filtering undissolved betaine and evaporating the filtrate to dryness.

Pharmaceutically suitable salts are those of sodium, potassium or calcium. The corresponding silver salts are obtained by reaction of an alkali metal or alkaline earth metal salt with a suitable silver salt such as silver nitrate.

The compositions according to the invention or the compounds on which they are based have a strong antibiotic action and exhibit, together with low toxicity, a wide antibacterial spectrum against Gram-positive and Gram-negative micro-organisms, in particular even against those which are resistant to various antibiotics, such as penicillins, cephalosporins, aminoglycosides, sulphonamides and tetracyclines.

These useful properties make possible their use as chemotherapeutic active compounds in medicine and veterinary medicine and as substances for the preservation of inorganic and organic materials, in particular of organic materials of all types, e.g. polymers, lubricants, dyes, fibres, leather, paper and wood, of foodstuffs and of water.

The compounds according to the invention are active against a very wide spectrum of microorganisms. Gram-negative and Gram-positive bacteria and bacteria-like microorganisms can be controlled using them and the diseases caused by these pathogens prevented, ameliorated and/or cured.

The active compounds have favourable toxicity to warm-blooded animals and are preferably suitable for the control of bacterial diseases which occur in productive, breeding, zoo, laboratory and experimental animals and pets in animal keeping and animal breeding. They are active here against all or individual stages of development and against resistant and normally sensitive strains. By control of the bacterial diseases, illness, cases of death and yield decreases (e.g. in the production of meat, milk, wool, hides, eggs, honey etc.) should be decreased, so that more economical and simpler animal keeping is possible as a result of the use of the active compounds.

The productive and breeding animals include mammals such as e.g. cattle, horses, sheep, pigs, goats, camels, water buffalo, donkeys, rabbits, fallow deer, reindeer, fur-bearing animals such as e.g. mink, chinchilla, racoon, birds such as e.g. hens, geese, turkeys, ducks, doves and species of bird for keeping at home and in zoos. They further include productive and ornamental fish.

The laboratory and experimental animals include mice, rats, guinea-pigs, golden hamsters, dogs and cats.

The pets include dogs and cats.

The fish include productive, breeding, aquarium and ornamental fish of all ages, which live in fresh and salt water. The productive and breeding fish include e.g. carp, eel, trout, whitefish, salmon, bream, roach, rudd, chub, sole, plaice, halibut, Japanese yellowtail (*Seriola quinqueradiata*), Japanese eel (*Anguilla japonica*), red seabream (*Pagurus major*), sea bass (*Dicentrarchus labrax*), grey mullet (*Mugilus cephalus*), pompano, gilthread seabream (*Sparus auratus*), Tilapia spp., Chichlidae species such as e.g. Plagioscion, channel catfish. The compositions according to the invention are particularly suitable for the treatment of fry, e.g. carp of 2–4 cm body length. The compositions are also very highly suitable in eel breeding.

Administration can be carried out both prophylactically and therapeutically.

Administration of the active compounds is carried out directly or preferably enterally in the form of suitable preparations.

Enteral administration of the active compounds is carried out, for example, orally in the form of powders, suppositories, tablets, capsules, pastes, drinks, granules, drenches, boli, medicated feed or drinking water.

Suitable preparations are:

solutions such as oral solutions, concentrates for oral administration after dilution;

emulsions and suspensions for oral semi-solid preparations;

solid preparations such as powders, premixes or concentrates, granules, pellets, tablets, boli, capsules.

Solutions are prepared by dissolving the active compound in a suitable solvent and possibly adding additives such as solubilizers, acids, bases, buffer salts, anti-oxidants or preservatives. The solutions are filtered and bottled.

Solvents which may be mentioned are: physiologically tolerable solvents such as water, alcohols such as ethanol, butanol, benzyl alcohol, glycerol, hydrocarbons, propylene glycol, polyethylene glycols, N-methyl-pyrrolidone, and mixtures thereof The active compounds can optionally also be dissolved in physiologically tolerable vegetable or synthetic oils.

Solubilizers which may be mentioned are: solvents which promote the solution of the active compound in the main solvent or prevent its precipitation. Examples are polyvinylpyrrolidone, polyethoxylated castor oil, polyethoxylated sorbitan esters.

Preservatives are: benzyl alcohol, trichlorobutanol, p-hydroxybenzoic acid esters, n-butanol.

Oral solutions are administered directly. Concentrates are administered orally after prior dilution to the administration concentration.

Colorants are all colorants permitted for use on animals and which can be dissolved or suspended.

Absorption-promoting substances are, for example, DMSO, spreading oils such as isopropyl myristate, dipropylene glycol pelargonate, silicone oils, fatty acid esters, triglycerides, fatty alcohols.

Antioxidants are sulphites or metabisulphites such as potassium metabisulphite, ascorbic acid, butylhydroxytoluene, butylhydroxyanisole, tocopherol.

Light screens are, for example, substances of the benzophenone or novantisolic acid class.

Orally administrable emulsions are either of the water-in-oil type or of the oil-in-water type.

They are prepared by dissolving the active compound either in the hydrophobic or in the hydrophilic phase and homogenizing this with the solvent of the other phase with the aid of suitable emulsifiers and optionally other auxiliaries such as colorants, absorption-promoting substances, preservatives, antioxidants, light screens and viscosity-increasing substances.

Hydrophobic phases (oils) which may be mentioned are: paraffin oils, silicone oils, natural vegetable oils such as sesame oil, almond oil, castor oil, synthetic triglycerides such as caprylic/capric acid bigylceride, triglyceride mixture with vegetable fatty acids of chain length $C_{8-12}$ or other specially selected natural fatty acids, partial glyceride mixtures of saturated or unsaturated fatty acids possibly also containing hydroxyl groups, mono- and diglycerides of $C_8/C_{10}$-fatty acids.

Fatty acid esters such as ethyl stearate, di-n-butyryl adipate, hexyl laurate, dipropylene glycol pelargonate, esters of a branched fatty acid of medium chain length containing saturated fatty alcohols of chain length $C_{16}$–$C_{18}$, isopropyl myristate, isopropyl palmitate, caprylic/capric acid esters of saturated fatty alcohols of chain length $C_{12}$–$C_{18}$, isopropyl stearate, oleyl oleate, decyl oleate, ethyl oleate, ethyl lactate, waxy fatty acid esters such as dibutyl phthalate, diisopropyl adipate, ester mixtures related to the latter, inter alia fatty alcohols such as isotridecyl alcohol, 2-octyldodecanol, cetylstearyl alcohol, oleyl alcohol.

Fatty acids such as e.g. oleic acid and their mixtures.

Hydrophilic phases which may be mentioned are: water, alcohols such as e.g. propylene glycol, glycerol, sorbitol and their mixtures.

Emulsifiers which may be mentioned are: non-ionic surfactants, e.g. polyethoxylated castor oil, polyethoxylated sorbitan monooleate, sorbitan monostearate, glyceryl monostearate, polyoxyethyl stearate, alkylphenol polyglycol ether; ampholytic surfactants such as di-Na N-lauryl-β-iminodipropionate or lecithin; anionic surfactants, such as Na laurylsulphate, fatty alcohol ether sulphates, mono/dialkyl polyglycol ether orthophosphoric acid ester monoethanolamine salt; cationic surfactants such as cetyltrimethylammonium chloride.

Other auxiliaries which may be mentioned are: viscosity-increasing and emulsion-stabilizing substances such as carboxymethylcellulose, methylcellulose and other cellulose and starch derivatives, polyacrylates, alginates, gelatine, gum arabic, polyvinylpyrrolidone, polyvinyl alcohol, copolymers of methyl vinyl ether and maleic anhydride, polyethylene glycols, waxes, colloidal silica or mixtures of the substances mentioned.

Suspensions are prepared by suspending the active compound in a vehicle, optionally with the addition of other auxiliaries such as wetting agents, colorants, absorption-promoting substances, preservatives, antioxidants light screens.

Vehicles which may be mentioned are all homogeneous solvents and solvent mixtures.

Wetting agents (dispersing agents) which may be mentioned are the surfactants indicated further above.

Further auxiliaries which may be mentioned are those indicated further above.

Semi-solid preparations differ from the suspensions and emulsions described above only by their higher viscosity.

For the production of solid preparations, the active compound is mixed with suitable excipients, optionally with the addition of auxiliaries, and brought into the desired form.

Excipients which may be mentioned are all physiologically tolerable solid inert substances. All such serve inorganic and organic substances. Inorganic substances are e.g. sodium chloride, carbonates such as calcium carbonate, hydrogen carbonates, aluminas, silicic acids, clays, precipitated or colloidal silica, phosphates.

Organic substances are e.g. sugar, cellulose, foodstuffs and feeds such as milk powder, animal meals, cereal flours and meals, starches.

Auxiliaries are preservatives, antioxidants and colorants which have already been mentioned above.

Other suitable auxiliaries are lubricants and glidants such as e.g. magnesium stearate, stearic acid, talc, bentonites, disintegration-promoting substances such as starch or crosslinked polyvinylpyrrolidone, binding agents such as e.g. starch, gelatine or linear polyvinylpyrrolidone, and dry binding agents such as micro-crystalline cellulose.

The active compounds can also be present in the preparations in a mixture with synergists or with other active compounds.

Ready-for-use preparations contain the active compound in concentrations of 10 ppm–20 percent by weight, preferably of 0.1–10 percent by weight.

Preparations which are diluted before use contain the active compound in concentrations of 0.5–90 percent by weight, preferably of 1 to 50 percent by weight.

In general, it has proven advantageous to administer amounts of about 0.5 to about 50 mg, preferably 1 to 20 mg, of active compound per kg of body weight per day to achieve effective results.

The active compounds can also be administered together with the feed or drinking water of the animals.

Feeds and foodstuffs contain 0.01 to 100 ppm, preferably 0.5 to 50 ppm, of the active compound in combination with a suitable edible material.

Such a feed and foodstuff can be used both for curative purposes and for prophylactic purposes.

Such a feed or foodstuff is prepared by mixing a concentrate or a premix which contains 0.5 to 30%, preferably 1 to 20% by weight, of an active compound in a mixture with an edible organic or inorganic carrier with customary feeds. Edible carriers are e.g. maize flour or maize and soya bean flour or mineral salts which preferably contain a small amount of an edible dust-preventing oil, e.g. maize oil or soya oil. The premix obtained in this process can then be added to the complete feed before feeding it to the animals.

The compounds according to the invention or the oily administrable compositions prepared therefrom are practically inactive in the customary in-vitro test systems for the determination of minimum inhibitory concentrations (MIC values) of antibacterial compounds. However, they are completely active if they are orally administered in-vivo.

EXAMPLE 1

Preparation of enrofloxacin N-oxide 20 g of enrofloxacin were suspended using 200 ml of demineralized water. 25 ml of $H_2O_2$ (30%) were added and the suspension was heated to reflux. After 3 to 4 hours, a yellow solution was formed from which crystals precipitated on cooling. White crystals were obtained by evaporating in a crystallizing dish.

Yield: 23.6 g of enrofloxacin N-oxide crude; contains <1% enrofloxacin or other by-products (HPLC).

EXAMPLE 2

20 g (55.7 mmol) of enrofloxacin are suspended in 180 ml of distilled water and 15 ml (0.147 mol) of 30% strength hydrogen peroxide are added. The mixture is then slowly heated to reflux. After 4 hours, it was cooled to room temperature, the solid was filtered off with suction is dried in a desiccator over sulphuric acid.

Yield: 19.37 g (92.7%) of enrofloxacin N-oxide

Content: 99.7%

Content of enrofloxacin: <0.1%

EXAMPLE 3

2 g (5.6 mmol) of enrofloxacin are dissolved in 20 ml of chloroform, then 1.2 g (5.6 mmol) of 80% strength 3-chloroperbenzoic acid are introduced. The mixture is stirred at room temperature until reaction is complete. The precipitate is filtered off with suction and dried.

Yield: 2.88 g (97%) of enrofloxacin 3-chlorobenzoate.

EXAMPLE 4

2 g (5.6 mmol) of enrofloxacin are suspended in 20 ml of acetonitrile then 0.7 ml (6.85 mmol) of 30% strength hydrogen peroxide are added. The mixture is then heated to reflux. After 6 hours, it is cooled and the precipitate is filtered off with suction.

EXAMPLE 5

2 g (5.6 mmol) of enrofloxacin are suspended in 18 ml of saturated sodium hydrogen carbonate solution and 1.5 ml (14.7 mmol) of 30% strength hydrogen peroxide are added. The mixture is then warmed to 50° C. After 90 minutes, it is cooled and adjusted to pH 6 using hydrochloric acid. The resulting precipitate is stirred at room temperature for two hours, then filtered off with suction and dried.

Danofloxacin N-oxide 10 g (0.028 mol) of danofloxacin are suspended in 90 ml of water, 7.5 ml (0.073 mol) of 30% hydrogen peroxide are added and the suspension is heated under reflux for 3 hours. Then 7.5 ml of 30% hydrogen peroxide are once again added and the suspension is heated under reflux for further 6 hours. Then it is cooled and the precipitate is filtered off with suction, washed with water and dried over sulphuric acid in a desiccator.

Yield: 0.71 g (79.3% of theory)

Purity: 95.1% (HPLC area)

The product was purified by suspending it in 150 ml of water with heating, allowing the suspension to cool and filtering off the precipitate.

Yield: 7.7 g (73% of theory)

Purity: 99.5% (HPLC area)

Content of danofloxacin: <0.1%

Melting point: 256° C. (with decomposition)

Marbofloxacin N-oxide 12.5 g (0.035 mol) of Marbofloxacin are suspended in 125 ml of a saturated $NaHCO_3$ solution, 9 ml (0.088 mol) of 30% hydrogen peroxide are added and the suspension is stirred for two hours at 50° C. The reddish-coloured solution is left to stand overnight at room temperature and is then adjusted to a pH of 6.5 with concentrated hydrochloric acid. The precipitated solid is filtered off with suction, washed with water and dried over sulphuric acid in a desiccator.

Yield: 11.71 g (88% of theory)

Purity: 98.5% (HPLC area)

Content of marbofloxacin: <0.1%

EXAMPLE A

Calves each having a weight of about 146 kg were treated as follows:

a) 4 animals received 5 mg/kg in each case of a 10% strength aqueous injection solution of enrofloxacin potassium salt intramuscularly a single time. After 0.5, 1, 2, 4, 6, 8, 24 hours p.i. blood was taken from the animals and the active compound level in the serum determined. From 0.5 to 24 hours p.i. the fully active dose of enrofloxacin could be detected in the serum.

b) 4 animals received 5 mg/kg in each case of a 10% strength aqueous injection solution of enrofloxacin N-oxide potassium salt intramuscularly a single time. After 0.5, 1, 2, 4, 6, 8, 24 hours p.i. blood was taken from the animals and the active compound level in the serum determined. From 0.5 to 24 hours p.i. no enrofloxacin could be detected in the serum (lower detection limit 0.01 μg/ml).

Melting point: 235° C. (with decomposition)

Ofloxacin N-oxide 8 g (0.022 mol) of ofloxacin are suspended in 80 ml of water, 5.9 ml (0.058 mol) of 30% hydrogen peroxide are added and the suspension is heated under reflux for one hour. The mixture is left to stand overnight. The precipitated solid is filtered off, washed with a small quantity of water and dried over sulphuric acid in a desiccator.

Yield: 8.30 g (quantitative)

Purity: 99% (HPLC area)

Content of ofloxacin: <0.1%

Melting point: 239° C. (with decomposition)

EXAMPLE B

Broilers each weighing approximately 350 g were treated as follows:

a) 24 animals were each given a single oral dose of 10 mg/kg of a 10% aqueous solution of the calcium salt of enrofloxacin. After intervals of 1, 2, 4, 6, 8 and 24 hours blood was taken from the animals and the content of active compound in the serum determined. The fully active dose of enrofloxacin was detected in the serum for a period of 1 to 24 hours p.a.

b) 18 animals were each given a single oral dose of 10 mg/kg of a 10% aqueous solution of enrofloxacin N-oxide. After intervals of 1, 2, 4, 6, 8 and 24 hours blood was taken from the animals and the active compound in the serum was determined. The fully active dose of enrofloxacin was detected in the serum for a period of 1 to 24 hours p.a.

What is claimed is:

1. Antibacterial compositions based on N-oxides of saturated nitrogen-containing heterocycles which are substituted by quinolone- or naphthyridonecarboxylic acids of the formula (I):

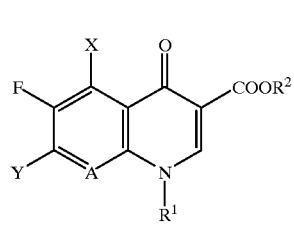

(I)

in which

X represents hydrogen, halogen, $C_{1-4}$-alkyl, $C_{1-4}$-alkoxy, $NH_2$,

Y represents radicals of the structures:

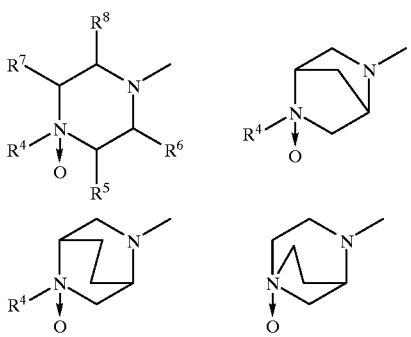

in which:

R⁴ represents straight-chain or branched $C_1$–$C_4$-alkyl which is optionally substituted by hydroxyl or methoxy, cyclopropyl, acyl having 1 to 3 C atoms, R⁵ represents hydrogen, methyl, phenyl, thienyl or pyridyl, R⁶ represents hydrogen or $C_{1-4}$-alkyl, R⁷ represents hydrogen or $C_{1-4}$-alkyl, R⁸ represents hydrogen or $C_{1-4}$-alkyl, and R¹ represents an alkyl radical having 1 to 3 carbon atoms, cyclopropyl, 2-flouroethyl, methoxy, 4-flourophenyl, 2,4-diflourophenyl or methylamino, R² represents hydrogen or alkyl having 1 to 6 carbon atoms, which is optionally substituted by methoxy or 2-methoxyethoxy, and cyclohexyl, benzyl, 2-oxopropyl, phenacyl, ethoxycarbonylmethyl, pivaloyloxymethyl, A represents nitrogen or =CH—, =C(halogen)—, =C(OCH₃)—, =C(CH₃)—, and their pharmaceutically utilizable hydrates, acid addition salts and salts with bases, excluding:

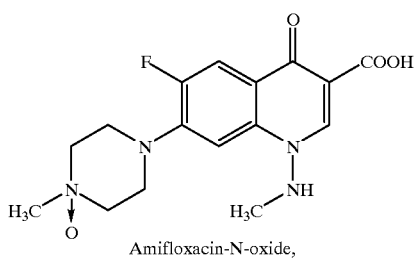
Amifloxacin-N-oxide,

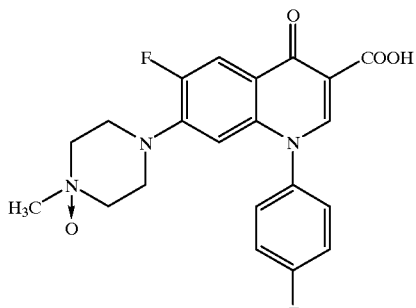
Difloxacin-N-oxide,

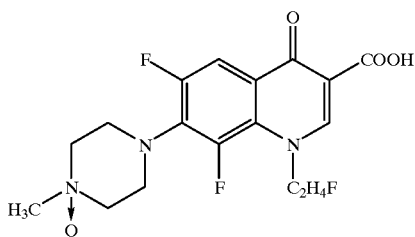
Fleroxacin-N-oxide and

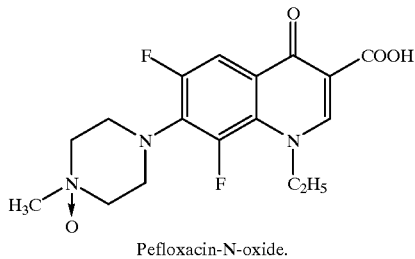
Pefloxacin-N-oxide.

2. Compounds of the formula (I) according to claim 1, in which:

A represents =CH—,

R¹ represents cyclopropyl,

R² represents hydrogen, methyl or ethyl

Y represents radicals of the structures:

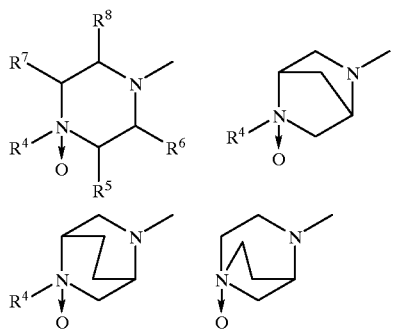

in which:

R⁴ represents methyl, ethyl which is optionally substitued by hydroxyl,

R⁵ represents hydrogen or methyl,

R⁷ represents hydrogen or methyl, and their pharmaceutically utilizable hydrates and acid addition salts, and the alkali metal, alkaline earth metal, silver and guanidinium salts of the carboxylic acids on which they are based.

3. Compound of the formula (I) according to claim 1, in which:

A represents =CH—,

R¹ represents cyclopropyl,

R² represents hydrogen, methyl or ethyl,

Y represents radicals of the structures:

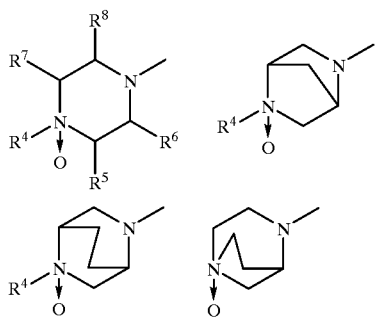

in which
R⁴ represents methyl, ethyl which is optionally substituted by hydroxyl,
R⁵ represents hydrogen or methyl,
R⁷ represents hydrogen or methyl, and their pharmaceutically utilizable hydrates and acid addition salts, and the alkali metal, alkaline earth metal, silver and guanidinium salts of the carboxylic acids on which they are based.

4. 4-Piperazinyl N-oxides of the active compounds enrofloxacin, marbofloxacin or ofloxacin.

5. A method of treating animals for bacterial disorders by administering to the animals a composition containing the compound of formula (I) as recited in claim 1 via drinking water or feed.

6. The method of claim 5 wherein the compound is administered via the feed.

7. Compositions administrable via the feed and drinking water of animals, based on N-oxides of saturated nitrogen-containing heterocycles which are substituted by quinolone- or naphthyridonecarboxylic acids, of the formulae (I):

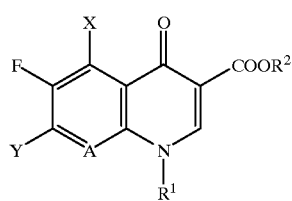

(I)

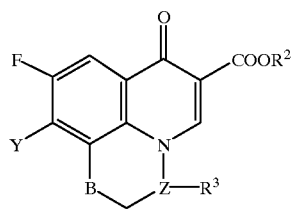

(II)

in which:

X represents hydrogen, halogen, $C_{1-4}$-alkyl, $C_{1-4}$-alkoxy, $NH_2$,

Y represents radicals of the structures:

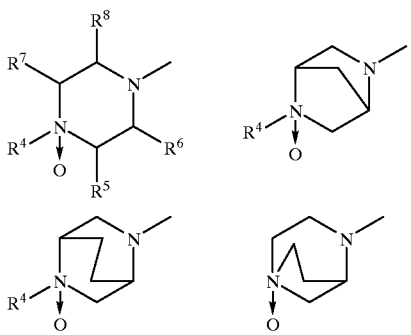

in which:
R⁴ represents straight-chain or branched $C_1$–$C_4$-alkyl which is optionally substituted by hydroxyl or methoxy, cyclopropyl; acyl having 1 to 3 C atoms,
R⁵ represents hydrogen, methyl, phenyl, thienyl or pyridyl,
R⁶ represents hydrogen or $C_{1-4}$-alkyl,
R⁷ represents hydrogen or $C_{1-4}$-alkyl,
R⁸ represents hydrogen or $C_{1-4}$-alkyl, and R¹ represents an alkyl radical having 1 to 3 carbon atoms, cyclopropyl, 2-fluoroethyl, methoxy, 4-fluorophenyl, 2,4-difluorophenyl or methylamino, R² represents hydrogen or alkyl having 1 to 6 carbon atoms, which is optionally substituted by methoxy or 2-methoxyethoxy, and cyclohexyl, benzyl, 2-oxopropyl, phenacyl, ethoxycarbonylmethyl, pivaloyloxymethyl, A represents nitrogen or =CH—, =C(halogen)—, =C(OCH₃), =C(CH₃)—, and their pharmaceutically utilizable hydrated, acid addition salts and salts with based, excluding:

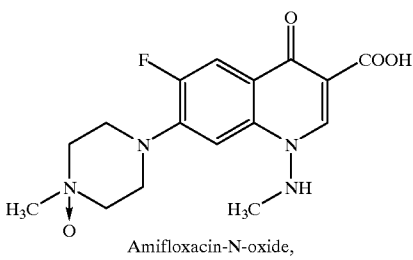

Amifloxacin-N-oxide,

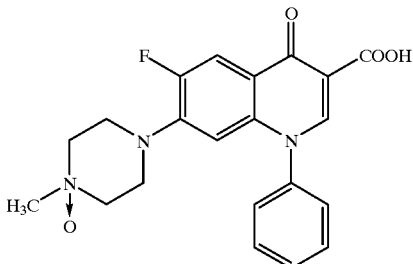

Difloxacin-N-oxide,

-continued

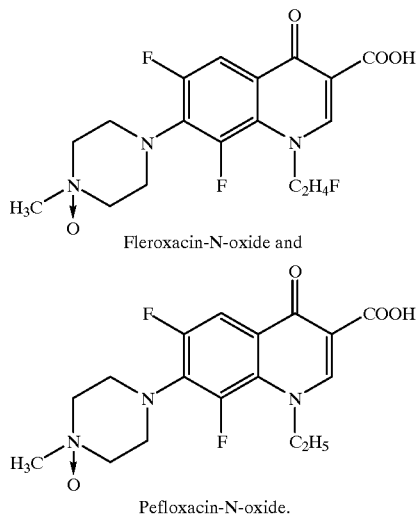

Fleroxacin-N-oxide and

Pefloxacin-N-oxide.

8. New N-oxides of saturated nitrogen-containing heterocycles which are substituted by quinolonecarboxylic acids, of the formula (Ia):

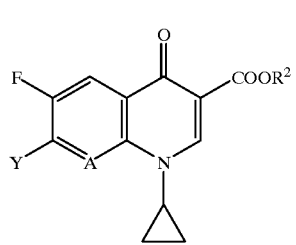

in which
Y represents radicals of the structures:

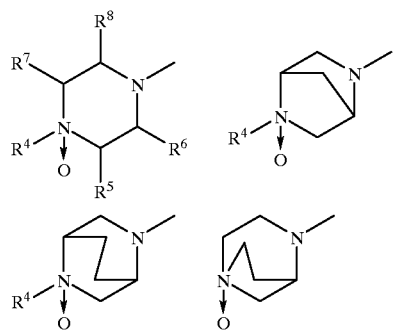

in which:
$R^4$ represents straight-chain or branched $C_1$–$C_4$-alkyl which is optionally substituted by hydroxyl or methoxy, cyclopropyl, acyl having 1 to 3 C atoms,
$R^5$ represents hydrogen, methyl, phenyl, thienyl or pyridyl, $R^6$ represents hydrogen or $C_{1-4}$-alkyl,
$R^7$ represents hydrogen or $C_{1-4}$-alkyl,
$R^8$ represents hydrogen or $C_{1-4}$-alkyl, and
$R^2$ represents hydrogen or alkyl having 1 to 4 carbon atoms, which is optionally substituted by methoxy and benzyl, 2-oxopropyl, phenacyl and also ethoxycarbonylmethyl, A represents =CH—, =C(halogen)— or =C(OCH$_3$)—, and their pharmaceutically utilizable hydrates or acid addition salts or salts with bases.

9. Process for the preparation of the compounds of the formula (Ia) according to claim 8, characterized in that:

a) the corresponding compounds (III):

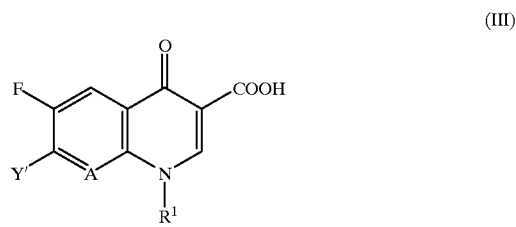

in which:
Y' represents the saturated nitrogen-containing heterocycle on which the N-oxide radicals Y are based,
A and $R^1$ have the meaning indicated in claim 8, are reacted with oxygen-donating agents, or when b) compounds of the formula (IV):

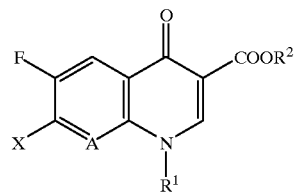

in which:
A, $R^1$, $R^2$ have the meaning indicated in claim 8 and
X denotes halogen, preferably fluorine or chlorine, are reacted with N-oxides of saturated nitrogen-containing heterocycles of the formula (V):

Y—H          (V)

in which
Y has the meaning indicated above, if appropriate in the presence of acid binders.

10. A process for producing a composition for bacterial disorders comprising incorporating the compound of formula (I) into drinking water or feed.

* * * * *